United States Patent
Johnson

[19]
[11] Patent Number: 6,123,079
[45] Date of Patent: Sep. 26, 2000

[54] ADJUSTABLE MALE CONDOM

[76] Inventor: Joseph T. Johnson, 8028 Regent Park La., Charlotte, N.C. 28210

[21] Appl. No.: 09/372,953

[22] Filed: Aug. 12, 1999

Related U.S. Application Data

[63] Continuation-in-part of application No. 09/123,656, Jul. 28, 1998, Pat. No. 5,934,054.
[51] Int. Cl.[7] ...................................................... A61F 6/04
[52] U.S. Cl. ........................................... 128/844; 128/918
[58] Field of Search .................................... 128/842, 844, 128/918; 604/347–353

[56] References Cited

U.S. PATENT DOCUMENTS

| | | | |
|---|---|---|---|
| 5,158,556 | 10/1992 | Starley | 128/842 |
| 5,314,447 | 5/1994 | Papurt | 128/844 |
| 5,327,911 | 7/1994 | Pien | 128/844 |
| 5,666,971 | 9/1997 | Anatolievich | 128/844 |
| 5,803,085 | 9/1998 | Asinousky | 128/844 |

*Primary Examiner*—Michael A. Brown
*Attorney, Agent, or Firm*—Christopher C. Dremann PC; Christopher C. Dremann

[57] ABSTRACT

An adjustable male condom securely retains the male condom on the penis of the wearer, thereby effectively preventing unwanted pregnancy and protecting against communicable diseases transmitted by the exchange of bodily fluids. The adjustable male condom includes a flaccid pouch made of an elastic, thin, disposable film material that is impervious to bodily fluids. The flaccid pouch includes an elongate, hollow, generally cylindrical body defining a longitudinal axis and having a first end and a closed second end. The adjustable male condom further includes a flaccid pouch harness attached to the first end of the body of the flaccid pouch. The flaccid pouch harness includes an annular retaining ring and a pair of elongate retaining straps. Each of the retaining straps has a first end attached to the retaining ring and a second end that remains unattached. Preferably, the retaining ring has a gap formed therein between the pair of retaining straps. In a preferred embodiment, the flaccid pouch harness further includes at least one grommet positioned on the pair of retaining straps for cinching the retaining straps tightly against the base of the wearer's penis or behind the scrotum of the wearer. The at least one grommet may have a single hole or a pair of holes formed therethrough for receiving the pair of retaining straps therein. Each of the retaining straps may also have a helical groove forming a helical ridge thereon for increasing the friction force between the grommet and the retaining straps.

17 Claims, 4 Drawing Sheets

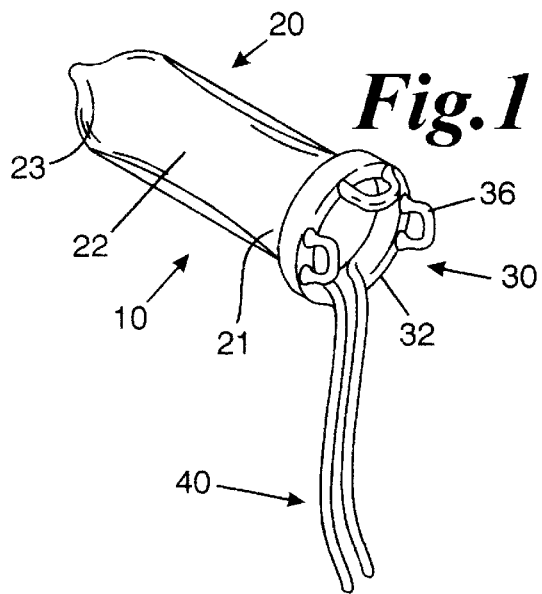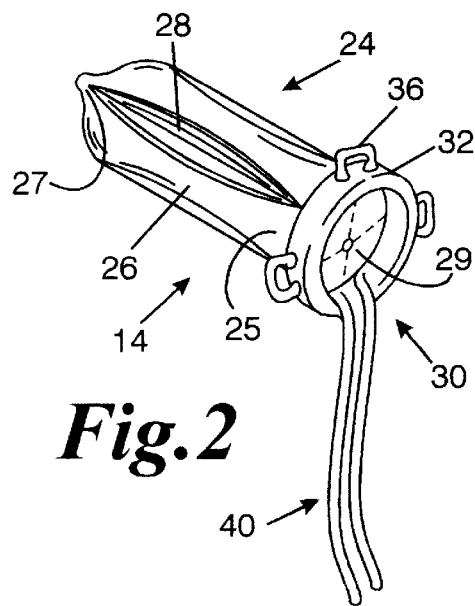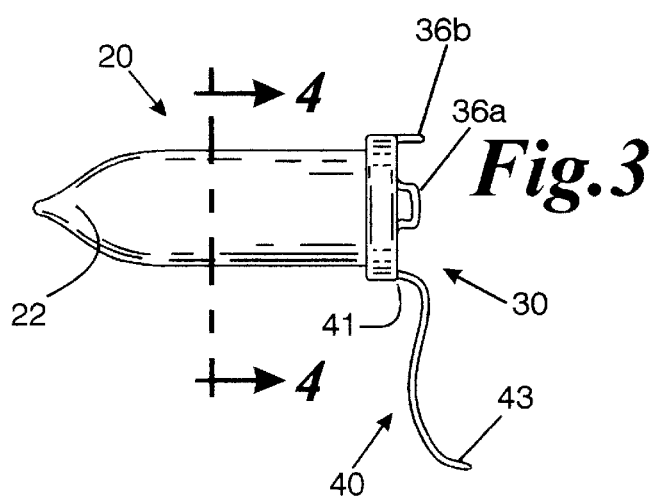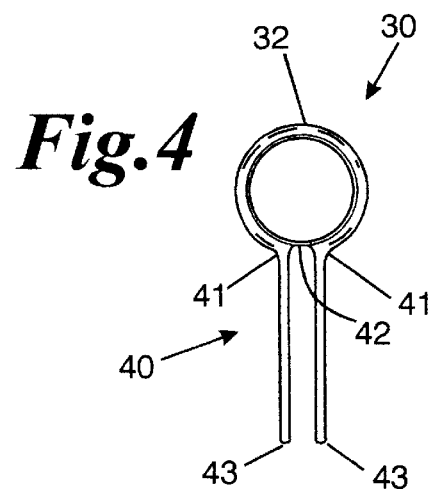

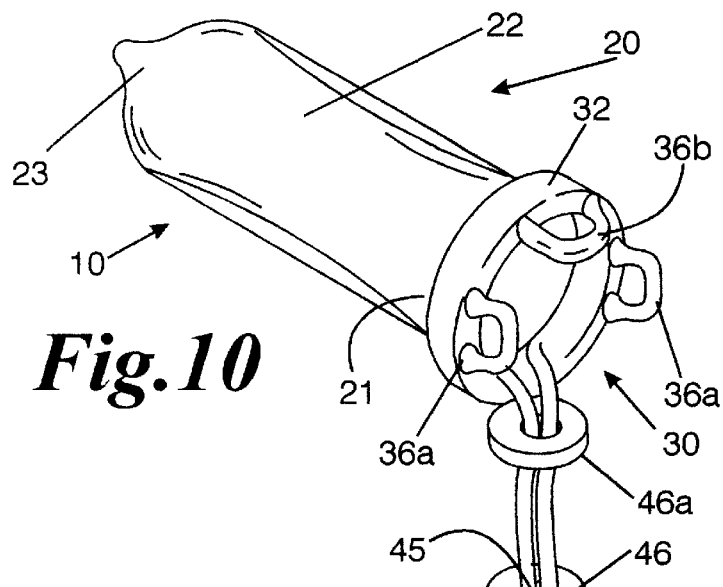
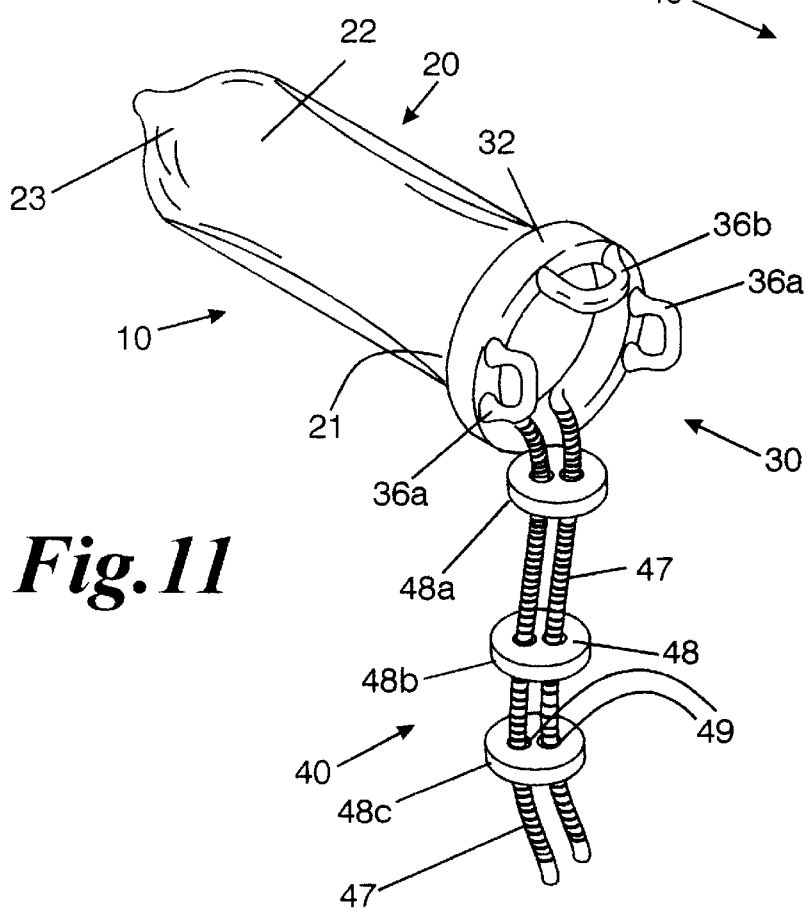

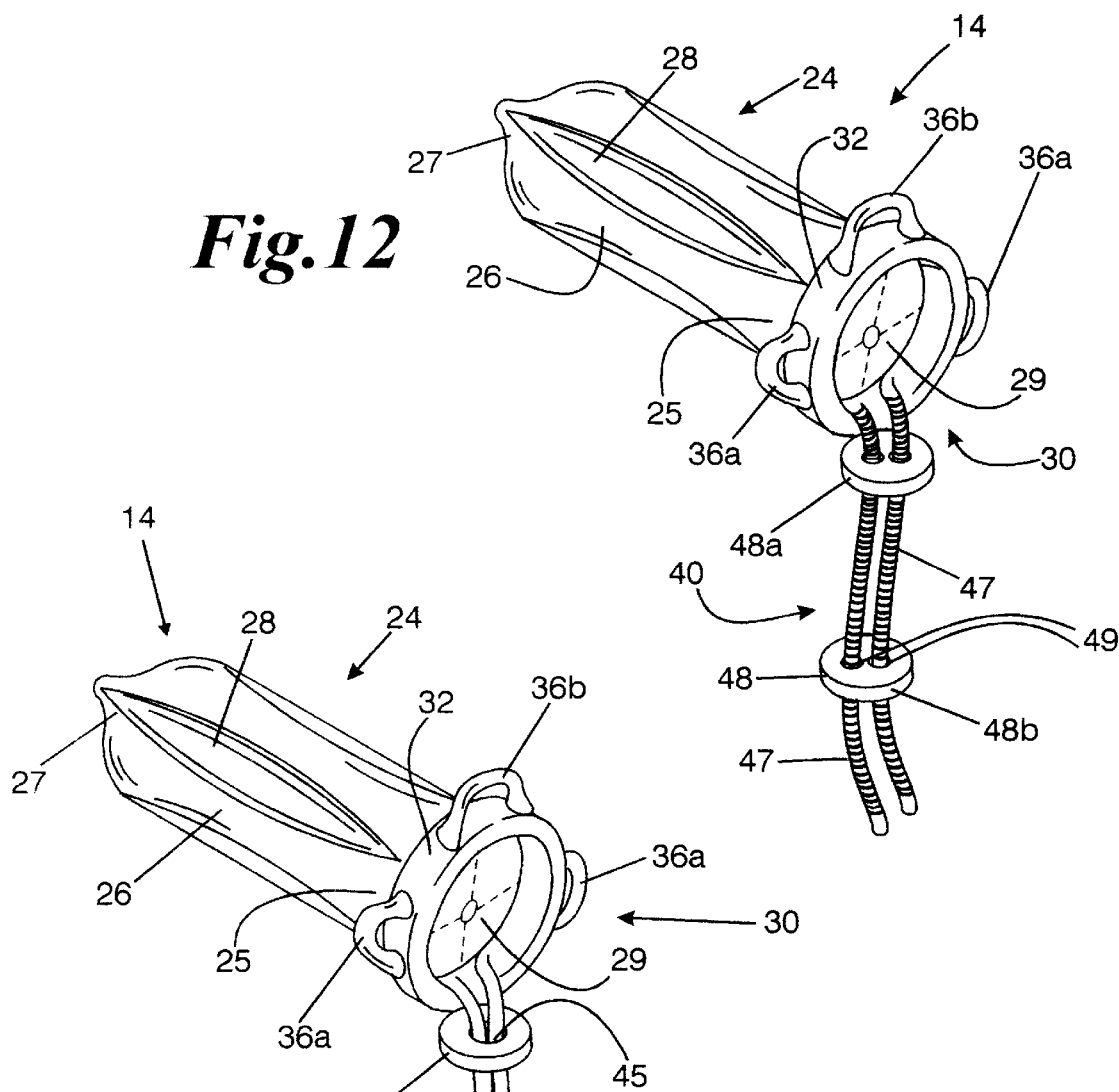

ADJUSTABLE MALE CONDOM

CROSS REFERENCE TO RELATED APPLICATION

This application is a continuation-in-part of U.S. patent application Ser. No. 09/123,656, filed Jul. 28, 1998, which issued Sep. 21, 1999, as U.S. Pat. No. 5,954,054.

FIELD OF THE INVENTION

The invention relates to an adjustable male condom that is designed and constructed to effectively prevent unwanted pregnancy and to protect the wearer against communicable diseases, including viral diseases such as Human Immunodeficiency Virus (HIV), which has been known to lead to the development of Acquired Immunodeficiency Syndrome (AIDS). The wearer of the adjustable male condom is also effectively protected against other Sexually Transmitted Diseases (STDs) such as herpes, syphilis and gonorrhea.

BACKGROUND OF THE INVENTION

Sexual partners have long been mindful of unwanted pregnancy. Meanwhile, the public at large has become increasingly fearful of contracting communicable diseases, such as HIV, AIDS and other STDs, from sexual activity. It is well known that pregnancy occurs when the male sperm comes into contact with the female egg. It is also known that STDs can be transmitted by the exchange of bodily fluids. Accordingly, the most widely used from of contraception and protection against STDs to date has been the male condom. Until now, however, there has not been a male condom that is highly effective in preventing unwanted pregnancy and at the same time guarding against the aforementioned public health concerns.

Known male condoms are primarily of two types. The first type consists of a thin, elongate, cylindrical body made of a form-fitting, fluid impervious material, such as latex, polyurethane or natural or synthetic rubber, which is open at one end and closed at the other end. The second type consists of a relatively thin, elongate, cylindrical body made of a loose-fitting, or "baggy", fluid impervious material, such as sheepskin or soft leather which is open at one end and closed at the other end. The condom is open at one end for insertion of the penis and is closed at the other end to maintain a fluid-tight barrier between the wearer'penis and the sex organ, typically the mouth, vagina or anus, of the wearer's partner. Ideally, the condom prevents male sperm and other bodily fluids from being exchanged during sexual activity. For one reason or another, however, the male condoms available today do not adequately prevent the exchange of bodily fluids during sexual activity, and thus do not adequately prevent unwanted pregnancy or the transmission of STDs.

The design and construction of the male condoms available today are not well adapted for their intended purpose. For example, the male condoms available today are generally difficult to properly apply to the penis of the wearer, particularly for those who are inexperienced or who may be under the influence of alcohol or drugs. If improperly applied, the condom may not provide an effective fluid-tight barrier, or worse yet, may become loose during the sexual activity, and rendered completely ineffective in preventing the exchange of bodily fluids. Even if properly applied to the penis of the wearer, known male condoms can be inadvertently removed during sexual activity if the condom is not securely retained on the wearer's penis. The likelihood that the condom will become loose or inadvertently removed is enhanced once the condom is subjected to the bodily fluids typically generated during sexual activity. Removal of the condom prior to completion of the sexual activity permits the bodily fluids of the wearer to come into contact with, and thus be exchanged with, the bodily fluids of the wearer's partner.

Another deficiency in the design and construction of known male condoms is that many do not include a spermicide of any kind. Those that do include a spermicide most often include one that is coated in the form of a dry film on the exterior surface of the condom. Others provide a separate spermicide to be mixed with a liquid or gel lubricant and applied on the exterior surface of the condom. Whether coated or mixed with a lubricant, the spermicide can be rubbed off as the condom is removed from its packaging or positioned on the wearer's penis. Further still, spermicides rapidly lose their effectiveness when exposed to the ambient atmosphere. Accordingly, the use of a male condom including a spermicide can be rendered ineffective unless the condom is used shortly after it is removed from its packaging, carefully positioned on the wearer's penis prior to the sexual activity and securely retained on the penis during the sexual activity.

It is therefore apparent that there exists a need for a male condom including a spermicide that is easy to properly apply and is adjustable to securely retain the condom on the penis of the wearer, thereby effectively preventing unwanted pregnancy and protecting against the transmission of STDs caused by the exchange of bodily fluids during sexual activity.

SUMMARY OF THE OBJECTS OF THE INVENTION

Accordingly, it is an object of the present invention to provide a male condom that is easy to properly apply to the wearer's penis prior to sexual activity.

It is a further object of the present invention to provide a male condom that is adjustable to securely retain the condom on the wearer's penis during sexual activity and immediately thereafter.

It is yet another object of the present invention to provide an adjustable male condom including a spermicide that is designed and constructed to be highly effective in preventing unwanted pregnancy as well as combating public health concerns, such as the transmission of STDs through the exchange of bodily fluids during sexual activity.

SUMMARY OF THE INVENTION

The invention is a male condom that is adjustable for securely retaining the condom on the wearer's penis, thereby effectively preventing unwanted pregnancy and protecting against communicable diseases transmitted by the exchange of bodily fluids. The adjustable male condom includes a flaccid pouch and a flaccid pouch harness integrally formed with the flaccid pouch. Preferably, the flaccid pouch is made of an elastic, thin, disposable film of fluid impervious material that forms an elongate, hollow, generally cylindrical body defining a longitudinal axis and having a first end and a second end. The body is open at the first end and is closed at the second end. In another preferred embodiment, the flaccid pouch further includes at least one longitudinally extending breakable-seal web formed on the exterior surface of the flaccid pouch. The breakable-seal web defines a hollow cavity for storing a liquid or gel lubricant or spermicide inside the web. The flaccid pouch may also include a breakable-seal entrance shield adjacent the first end of the body for storing a liquid or gel lubricant or spermicide inside the body.

The flaccid pouch harness is likewise preferably made of an elastic, disposable film of fluid impervious material that is substantially thicker than the tin, disposable film of the flaccid pouch. The flaccid pouch harness includes an annular retaining ring attached to the flaccid pouch adjacent the first end. The flaccid pouch harness further includes at least one application handle depending outwardly from the retaining ring. The flaccid pouch harness further includes a pair of thin, elongate retaining straps extending from the retaining ring. The first end of each retaining strap is attached to the retaining ring and the second end of each retaining strap remains unattached, for a purpose to be described hereinafter.

In a preferred embodiment, the at least one application handle of the flaccid pouch harness extends radially and depends outwardly from the exterior surface of the retaining ring. In another preferred embodiment, the at least one application handle of the flaccid pouch harness extends longitudinally and depends generally rearwardly from the exterior surface of the retaining ring. The at least one application handle may have any convenient configuration, but preferably is formed in a closed loop having a pair of opposed ends integrally formed with the retaining ring. Preferably, the at least one application handle includes a plurality of application handles that are circumferentially spaced about the retaining ring. For example, in one embodiment, the plurality of application handles includes a pair of diametrically opposed application handles. In an alternative embodiment, the plurality of application handles further includes a third application handle positioned medially between the pair of diametrically opposed application handles. In yet another embodiment, the plurality of application handles includes a first pair of diametrically opposed application handles and a second pair of diametrically opposed application handles positioned generally perpendicular to the first pair of diametrically opposed application handles.

The pair of retaining straps attached to the retaining ring are utilized to securely retain the male condom on the penis of the wearer. The retaining straps may be tied together in a tight knot below or above the base of the wearer's penis. Alternatively, the retaining straps may be wrapped around the wearer's scrotum from above or below the base of the penis and then tied together in a tight knot behind the wearer's scrotum. Alternatively, the retaining straps may be wrapped around the wearer's scrotum from below the base of the penis and back around the scrotum, and then tied together in a tight know above the base of the wearer's penis. In a preferred embodiment, the retaining straps also include at least one grommet having at least one opening therethrough for positioning the grommet on both retaining straps. The at least one grommet is utilized to cinch the retaining straps against the wearer's penis or scrotum prior to tying the retaining straps in a tight knot. In an alternative embodiment, the retaining straps have a helical groove forming a helical ridge thereon for engaging the at least one grommet. In other preferred embodiments, the retaining straps include two or three grommets for cinching the retaining straps below the wearer's penis, behind the wearer's scrotum or above the wearer's penis, as applicable.

BRIEF DESCRIPTION OF THE DRAWINGS

In view of the above and other objects which will more readily appear as the nature of the invention is better understood, the invention consists in the novel combination and arrangement of parts hereinafter more fully described, illustrated and claimed with reference being made to the attached drawings in which:

FIG. 1 is a perspective view of a preferred embodiment of an adjustable male condom according to the invention;

FIG. 2 is a perspective view of another preferred embodiment of an adjustable male condom according to the invention including a longitudinally extending breakable-seal web;

FIG. 3 is a side elevation view of the adjustable male condom of FIG. 1;

FIG. 4 is a sectional view of the adjustable male condom of FIG. 1 taken along the line 4—4 in FIG. 3;

FIG. 10 is a perspective view of the adjustable male condom of FIG. 1 including at least one grommet for cinching the retaining straps of the flaccid pouch harness against the penis and scrotum of the wearer;

FIG. 11 is a perspective view of an alternative embodiment of the adjustable male condom of FIG. 10;

FIG. 12 is a perspective view of the adjustable male condom of FIG. 2 including at least one grommet for cinching the retaining straps of the flaccid pouch harness against the penis and scrotum of the wearer; and FIG. 13 is a perspective view of an alternative embodiment of the adjustable male condom of FIG. 12.

DETAILED DESCRIPTION OF THE PREFERRED EMBODIMENTS

Figure 5:
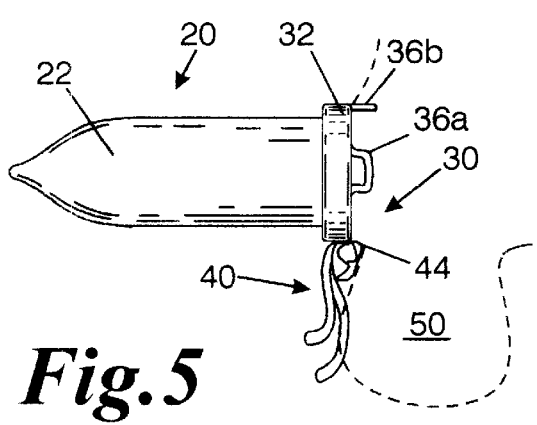
FIG. 5 is a side elevation view of the adjustable male condom of FIG. 1 illustrating a preferred method of securely retaining the condom on the penis of the wearer.

Preferred embodiments of the present invention will be described more fully hereafter followed by a brief description of a number of alternative preferred embodiments. However, the invention should not be construed as being limited by the preferred embodiments described herein. Rather, it is intended that the invention be construed broadly to encompass any and all embodiments of an adjustable male condom having the features described and illustrated herein which is within the skill of a person of ordinary skill in the relevant art. In the description, like reference numerals designate like or corresponding parts throughout the several figures. It is also to be understood that positional terms such as "top", "bottom", "side", "front" and "rear" are used in the description for purposes of locating one element relative to another, and thus, are not to be construed as limiting terms. Finally, it should be understood that the illustrations provided in the figures are for the purpose of describing preferred embodiments of the invention, and thus, are not intended to limit the invention in any manner.

Referring now to the accompanying figures, the invention is an adjustable male condom, indicated generally at 10, 14 for preventing unwanted pregnancy and for protecting against the transmission of STDs, such as AIDS, through the exchange of bodily fluids, such as saliva, perspiration, sperm and blood, during sexual activity. In the broadest sense, the adjustable male condom 10, 14 comprises a flaccid pouch 20, 24 and a flaccid pouch harness 30. The flaccid pouch harness comprises an annular retaining ring 32 and at least one application handle 36 depending outwardly from the retaining ring. The flaccid pouch harness further comprises a pair of retaining straps 40 each having a first end 41 attached to the retaining ring 32 and a second end 43 opposite the first end that remains unattached for a purpose to be described hereinafter.

A preferred embodiment of an adjustable male condom 10 according to the invention is shown in FIG. 1. The flaccid pouch 20 of the adjustable male condom 10 is a form-fitting pouch, such as a conventional "roll-on" condom, made of an elastic, thin, disposable film material. More preferably, the flaccid pouch 20 is made of a dipped or molded, uninterrupted liquid latex, liquid polyurethane or natural or synthetic rubber that is impervious to fluids, and in particular, to male sperm and other bodily fluids that transmit liquid-born viruses, such STDs. The flaccid pouch 20 forms an elongate, hollow, generally cylindrical body 22 defining a longitudinal axis and having a first end 21 and a second end 23. The body 22 is closed at the second end 23 and is open at the first end 21. As previously mentioned, the adjustable male condom 10 further comprises a flaccid pouch harness 30 and a pair of retaining straps 40, both which will be described in greater detail hereinafter.

Another preferred embodiment of an adjustable male condom 14 according to the invention is shown in FIG. 2. The flaccid pouch 24 of the adjustable male condom 14 of FIG. 2 is a loose-fitting condom, such as a conventional "baggy" condom made of a somewhat elastic, thin, disposable film material. More preferably, the flaccid pouch 24 is made of a natural or synthetic sheepskin or leather. The flaccid pouch 24 forms an elongate, hollow, generally cylindrical body 26 defining a longitudinal axis and having a first end 25 and a second end 27. The body 26 is closed at the second end 27 and may be closed at the first end 25 prior to use, as will be described, and is open at the first end 25 during use. The flaccid pouch 24 comprises at least one longitudinally extending breakable-seal web 28 formed on the exterior surface of the flaccid pouch. An example of such a breakable-seal web is described and shown in U.S. patent application Ser. No. 09/123,656, now U.S. Pat. No. 5,954, 054, the disclosure of which is incorporated herein by reference. The breakable-seal web 28 defines a hollow cavity for storing a liquid or gel lubricant or spermicide inside the web. The flaccid pouch may also include a breakable-seal entrance shield 29 adjacent the first end 25 of the body 26. An example of such a breakable-seal entrance shield is disclosed and shown in U.S. patent application Ser. No. 09/123,656, now U.S. Pat. No. 5,599,054. Likewise, the breakable-seal entrance shield 29 stores a liquid or gel lubricant or spermicide inside the body 26. Both the breakable-seal web 28 and the breakable-seal entrance shield 29 are opened as the penis of the wearer is inserted into the flaccid pouch 24 to release the lubricant or spermicide.

The flaccid pouch harness 30 is made of an elastic, disposable material that is substantially thicker than the thin, disposable film material of the flaccid pouch 20, 24 of the adjustable male condom 10, 14. Preferably, the flaccid pouch harness 30 is made of a dipped or molded, uninterrupted liquid latex, liquid polyurethane or natural or synthetic rubber material that is impervious to fluids, and in particular is impervious to male sperm and to other bodily fluids that transmit liquid-born viruses, such as STDs. As previously mentioned, the flaccid pouch harness 30 comprises an annular retaining ring 32. The retaining ring 32 protects the relatively fragile flaccid pouch 20, 24 against ripping or tearing adjacent the first end 21, 25 as the adjustable male condom 10, 14 is positioned on the penis of the wearer. The retaining ring 32 also protects the flaccid pouch 20, 24 from ripping or tearing adjacent the first end 21, 25 during use. The reduced diameter elastic retaining ring 32 also applies pressure to the base of the penis of the wearer, thereby holding the adjustable male condom 10, 14 on the penis more securely. Thus, it is less likely that the adjustable male condom 10, 14 will be inadvertently removed during sexual activity.

As previously mentioned, the flaccid pouch harness 30 further comprises at least one application handle 36. An example of such an application handle 36 is described and shown in greater detail in U.S. patent application Ser. No. 09/123,656, now U.S. Pat. No. 5,954,054. The application handle 36 may have any convenient configuration, but preferably is formed in a closed loop having a pair of opposed ends integrally formed with the retaining ring 32. The application handle 36 permits the adjustable male condom 10, 14 to be properly positioned on the penis of the wearer. Use of the application handle 36 also protects the relatively fragile flaccid pouch 20, 24 against ripping or tearing adjacent the first end 21, 25 as the adjustable male condom 10, 14 is positioned on the penis of the wearer. The application handle 36 may also be utilized to release air that is trapped inside the cavity defined by the body 22, 26 of the flaccid pouch 20, 24 when the adjustable male condom 10, 14 is positioned on the penis of the wearer. The application handle 36 is pulled outwardly to temporarily create a space between the retaining ring 32 and the wearer's penis for evacuating any air trapped inside the cavity. Accordingly, the adjustable male condom 10, 14 is further secured on the penis of the wearer. Thus, it is less likely that the adjustable male condom 10, 14 will be inadvertently removed during sexual activity.

In the preferred embodiment of the adjustment male condom 10 shown in FIG. 1, the at least one application handle 36 extends radially and depends outwardly from the exterior surface of the retaining ring 32. In the preferred embodiment of the adjustable male condom 14 shown in FIG. 2, the at least one application handle 36 extends longitudinally and depends generally rearwardly from the exterior surface of the retaining ring 32. Preferably, the flaccid pouch harness 30 comprises a plurality of application handle 36 circumferentially spaced about the retaining ring 32. In the preferred embodiments shown herein, the plurality of application handles comprises three application handles 36 consisting of a pair of diametrically opposed application handles 36a and a third application handle 36b positioned medially between the application handles 36a. However, the plurality of application handles 36 may, for example, consist of a pair of diametrically opposed application handles 36a, or a pair of diametrically opposed application handles 36a and a pair of diametrically opposed application handles 36b.

As previously mentioned, the flaccid pouch harness 30 further comprises a pair of retaining straps 40. Each of the retaining straps 40 has a first end 41 attached to the retaining ring 32 and a second end 43 that remains unattached. Preferably, the pair of retaining straps 40 are integrally formed with the retaining ring 32. As best shown in FIGS. 3 and 4, the pair of retaining straps 40 preferably depend outwardly from the retaining ring 32 at a location opposite the medial application handle 36b. A recess, or gap 42 (FIG. 4), is formed in the retaining ring 32 such that the pair of retaining straps 40 close the gap 42, and thereby constrict the retaining ring on the wearer's penis, when the retaining straps are tied together in a tight knot. Thus, the adjustable male condom 10, 14 is further secured on the penis of the wearer so that it is less likely that the adjustable male condom will be inadvertently removed during sexual activity.

Figure 6:
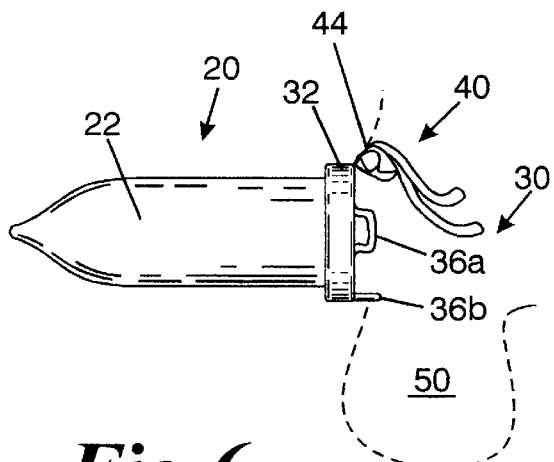
FIG. 6 is a side elevation view of the adjustable male condom of FIG. 1 illustrating an alternative method of securely retaining the condom on the penis of the wearer.
Figure 7:
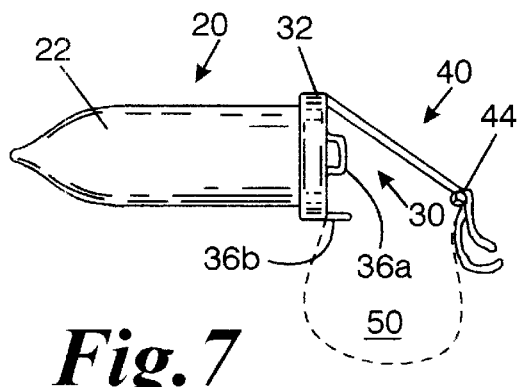
FIG. 7 is a side elevation view of the adjustable male condom of FIG. 1 illustrating another alternative method of securely retaining the condom on the penis of the wearer.
Figure 8:
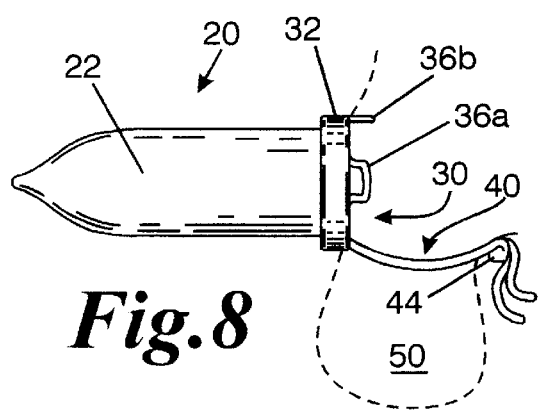
FIG. 8 is a side elevation view of the adjustable male condom of FIG. 1 illustrating another alternative method of securely retaining the condom on the penis of the wearer.
Figure 9:
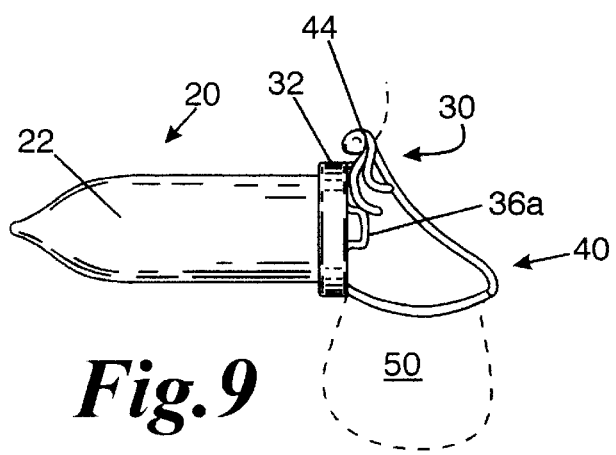
FIG. 9 is a side elevation view of the adjustable male condom of FIG. 1 illustrating another alternative method of securely retaining the condom on the penis of the wearer.

Obviously, the pair of retaining straps 40 can be tied together in a number of different ways to further secure the adjustable male condom 10, 14 on the penis of the wearer. Various methods of typing the pair of retaining straps 40 together in a tight knot 44 are illustrated in FIGS. 5–9. In FIG. 5, the pair of retaining straps 40 are tied together below the base of the penis adjacent the scrotum 50 of the wearer. In FIG. 6, the pair of retaining straps 40 are tied together above the base of the penis opposite the scrotum 50 of the wearer. In FIG. 7, the pair of retaining straps 40 are wrapped around the scrotum 50 of the wearer from above the base of the penis in opposite directions and tied together behind the scrotum. In FIG. 8, the pair of retaining straps 40 are wrapped around the scrotum 50 of the wearer from below the base of the penis in opposite directions and tied together behind the scrotum. In FIG. 9, the pair of retaining straps 40 are wrapped around the scrotum 50 of the wearer from below the base of the penis in opposite directions, crossed over, wrapped around the scrotum again in opposite directions and then tied together above the base of the penis.

In an alternative embodiment shown in FIG. 10, the flaccid pouch harness 30 further comprises at least one grommet 56 for further securing the adjustable male condom 10 on the penis of the wearer, The at least one grommet 46 is positioned on the pair of retaining straps 40 by inserting the retaining straps into a single hole 45 formed through the grommet. The at least one grommet 46 is then moved along the pair of retaining straps 40 in the direction of the retaining ring 32 to cinch the retaining straps against the base of the penis or behind the scrotum 50, as applicable, thereby further securing the adjustable male condom 10 on the penis of the wearer in the manner illustrated in FIGS. 5–9. In particular, the flaccid pouch harness 30 shown in FIG. 10 comprises three grommets 46. A first grommet 46a cinches the retaining straps 40 below the base of the wearer's penis, a second grommet 46b cinches the retaining straps 40 behind the wearer's scrotum and a third grommet 46c cinches the retaining straps 40 above the base of the wearer's penis in the manner illustrated in FIG. 9.

In the alternative embodiment shown in FIG. 11, the flaccid pouch harness 30 further comprises at least one grommet 48 for further securing the adjustable male condom 10 on the penis of the wearer. In addition, each of the pair of retaining straps 40 has a continuous, helical groove forming a helical ridge 47 thereon. The ridge 47 creates an increased friction force between the at least one grommet 48 and the retaining straps 40. The at least one grommet 48 is positioned on the pair of retaining straps 40 by inserting the retaining straps into a pair of holes 49 formed through the grommet. The at least one grommet 48 is then moved along the pair of retaining straps 40 in the direction of the retaining ring 32 to cinch the retaining straps against the base of the penis or behind the scrotum 50, as applicable, thereby further securing the adjustable male condom 10 on the penis of the wearer in the manner illustrated in FIGS. 5–9. In particular, the flaccid pouch harness 30 shown in FIG. 11 comprises three grommets 48. A first grommet 48a cinches the retaining straps 40 below the base of the wearer's penis, a second grommet 48b cinches the retaining straps 40 behind the wearer's scrotum and a third grommet 48c cinches the retaining straps 40 above the base of the wearer's penis in the manner illustrated in FIG. 9.

In the alternative embodiment shown in FIG. 12, the flaccid pouch harness 30 further comprises at least one grommet 48 for further securing the adjustable male condom 14 on the penis of the wearer. In addition, each of the pair of retaining straps 40 has a continuous, helical groove forming a helical ridge 47 thereon. The ridge 47 creates an increased friction force between the at least one grommet 48 and the retaining straps 40. The at least one grommet 48 is positioned on the pair of retaining straps 40 by inserting the retaining straps into a pair of holes 49 formed through the grommet. The at least one grommet 48 is then moved along the pair of retaining straps 40 in the direction of the retaining ring 32 to cinch the retaining straps against the base of the penis or behind the scrotum 50, as applicable, thereby further securing the adjustable male condom 10 on the penis of the wearer in the manner illustrated in FIGS. 5–9. In particular, the flaccid pouch harness 30 shown in FIG. 12 comprises two grommets 48. A first grommet 48a cinches the retaining straps 40 below the base of the wearer's penis and a second grommet 48b cinches the retaining straps 40 behind the wearer's scrotum in the manner illustrated in FIG. 8.

In the alternative embodiment shown in FIG. 13, the flaccid pouch harness 30 further comprises at least one grommet 46 for further securing the adjustable male condom 14 on the penis of the wearer. The at least one grommet 46 is positioned on the pair of retaining straps 40 by inserting the retaining straps into a single hole 45 formed through the grommet. The at least one grommet 46 is then moved along the pair of retaining straps 40 in the direction of the retaining ring 32 to cinch the retaining straps against the base of the penis or behind the scrotum 50, as applicable, thereby further securing the adjustable male condom 14 on the penis of the wearer in the manner illustrated in FIGS. 5–9. In particular, the flaccid pouch harness 30 shown in FIG. 13 comprises two grommets 46. A first grommet 46a cinches the retaining straps 40 below the base of the wearer's penis and a second grommet 46b cinches the retaining straps 40 behind the wearer's scrotum in the manner illustrated in FIG. 8.

From the forgoing, it is readily apparent that the present invention provides an adjustable male condom that is easy to properly apply prior to sexual activity and is securely retained on the penis of the wearer before, during and after sexual activity, thereby effectively preventing unwanted pregnancy as well as combating public health concerns. It is to be understood that the forgoing description and specific embodiments shown herein are merely illustrative of the best mode of the invention and the principals thereof, and that various modifications and additions may be made by those skilled in the art without departing unnecessarily from the spirit and scope of the invention, which is intended to be limited only by the scope of the appended claims.

That which is claimed is:

1. An adjustable male condom for preventing unwanted pregnancy and protecting against communicable diseases transmitted by the exchange of bodily fluids, said adjustable male condom comprising:

a flaccid pouch comprising an elongate, hollow, generally cylindrical body defining a longitudinal axis and having a first end and a second end; and a flaccid pouch harness comprising
  an annular retaining ring attached to the first end of said flaccid pouch;
  a pair of elongate retaining straps, each of said pair of retaining straps having a first end attached to said retaining ring and a second end that remains unattached; and
  at least one grommet positioned on said pair of retaining straps.

2. An adjustable male condom according to claim 1 wherein said at least one grommet has a single hole formed therethrough for receiving said pair of retaining straps therein.

3. An adjustable male condom according to claim 1 wherein said at least one grommet has a pair of holes formed therethrough for receiving said pair of retaining straps therein.

4. An adjustable male condom according to claim 1 wherein each of said pair of retaining straps has a helical groove forming a helical ridge thereon.

5. An adjustable male condom according to claim 1 wherein said retaining ring has a gap formed therein medially between said pair of retaining straps.

6. An adjustable male condom according to claim 1 wherein said flaccid pouch harness further comprises at least one application handle attached to said retaining ring.

7. An adjustable male condom according to claim 6 wherein said at least one application handle extends radially and depends generally outwardly from the exterior surface of said retaining ring.

8. An adjustable male condom according to claim 6 wherein said at least one application handle extends longitudinally and depends generally rearwardly from the exterior surface of said retaining ring.

9. An adjustable male condom according to claim 6 wherein said at least one appliction handle is formed in a closed loop.

10. An adjustable male condom according to claim 6 wherein said at least one application handle comprises a plurality of application handles circumferentially spaced about said retaining ring.

11. An adjustable male condom according to claim 10 wherein said plurality of application handles consists of a pair of diametrically opposed application handles and an application handle positioned medially between said pair of application handles.

12. An adjustable male condom according to claim 1 wherein said flaccid pouch is made of an elastic, thin, disposable film material that is impervious to bodily fluids.

13. An adjustable male condom according to claim 12 wherein said flaccid pouch is made of a material selected from the group consisting of liquid latex, polyurethane, natural rubber, synthetic rubber, sheepskin and leather.

14. An adjustable male condom according to claim 12 wherein said flaccid pouch harness is made of an elastic, disposable material that is impervious to bodily fluids and that is substantially thicker than the elastic, thin, disposable film material of said flaccid pouch.

15. An adjustable male condom for preventing unwanted pregnancy and protecting against communicable diseases transmitted by the exchange of bodily fluids, said adjustable male condom comprising
  a flaccid pouch comprising
    an elongate, hollow, generally cylindrical body defining a longitudinal axis and having a first end and a second end; and
    at least one longitudinally extending, breakable-seal web defining a cavity adjacent the exterior surface of said body wherein said breakable-seal web opens longitudinally along its entire length to release a lubricant; and
  a flaccid pouch harness comprising
    an annular retaining ring attached to the first end of said flaccid pouch; and
    a pair of elongate retaining straps, each of said pair of retaining straps having a first end attached to said retaining ring and a second end that remains unattached.

16. An adjustable male condom according to claim 15 wherein the diameter of said body of said flaccid pouch is less than the diameter of a form-fitting male condom and expands to a diameter that is greater than the diameter of a form-fitting male condom when said at least one breakable-seal web is broken.

17. An adjustable male condom for preventing unwanted pregnancy and protecting against communicable diseases transmitted by the exchange of bodily fluids, said adjustable male condom comprising
  a flaccid pouch comprising
    an elongate, hollow, generally cylindrical body defining a longitudinal axis and having a first end and a second end; and
    a breakable-seal entrance shield adjacent the first end of said body for temporarily closing said body at said first end; and
  a flaccid pouch harness comprising
    an annular retaining ring attached to the first end of said flaccid pouch; and
    a pair of elongate retaining straps, each of said pair of retaining straps having a first end attached to said retaining ring and a second end that remains unattached.

* * * * *